(12) United States Patent
Maksoud (10) Patent No.: US 11,186,925 B2
(45) Date of Patent: Nov. 30, 2021

(54) SYSTEM FOR NANO-COATING A SUBSTRATE

(71) Applicant: Fouad Junior Maksoud, Shouf (LB)

(72) Inventor: Fouad Junior Maksoud, Shouf (LB)

( * ) Notice: Subject to any disclaimer, the term of this patent is extended or adjusted under 35 U.S.C. 154(b) by 50 days.

(21) Appl. No.: 16/650,365

(22) PCT Filed: Sep. 27, 2017

(86) PCT No.: PCT/US2017/053731
§ 371 (c)(1),
(2) Date: Mar. 24, 2020

(87) PCT Pub. No.: WO2019/066808
PCT Pub. Date: Apr. 4, 2019

(65) Prior Publication Data
US 2020/0232122 A1 Jul. 23, 2020

(51) Int. Cl.
*B05B 5/08* (2006.01)
*B05B 14/00* (2018.01)
(Continued)

(52) U.S. Cl.
CPC ........... *D01D 5/0069* (2013.01); *B05B 5/082* (2013.01); *B05B 16/90* (2018.02); *B05D 1/045* (2013.01); *D01D 5/003* (2013.01); *D01D 5/0038* (2013.01); *D01D 5/0061* (2013.01); *D01D 5/0076* (2013.01); *D04H 1/728* (2013.01);
(Continued)

(58) Field of Classification Search
CPC ........... B05B 5/08; B05B 5/082; B05B 14/00; B05B 16/00; B05B 16/40; B05B 16/90; B05D 1/04; B05D 1/045; D01D 5/003; D01D 5/0038; D01D 5/0061; D01D 5/0069; D01D 5/0076; D01D 5/0084
USPC ...... 264/37.18, 37.26, 129, 171.1, 257, 258, 264/464, 465, 466, 484; 425/113, 114, 425/174.8 E, 215, 377, 382.2; 427/477, 427/478, 479, 481, 485; 118/621, 628
See application file for complete search history.

(56) References Cited

U.S. PATENT DOCUMENTS 6,713,011 B2 3/2004 Chu et al.
8,568,587 B2 10/2013 Olesik et al.
(Continued)

FOREIGN PATENT DOCUMENTS

GB 1133710 A 11/1968
WO 2009102365 A2 8/2009
WO 2014160045 A1 10/2014

*Primary Examiner* — Leo B Tentoni
(74) *Attorney, Agent, or Firm* — Nath, Goldberg & Meyer; Richard C. Litman (57) ABSTRACT

The system for nano-coating a substrate (10) includes a housing (12) having an upper, dispensing chamber (18) in which electrospraying or electrospinning can occur, a lower storage chamber, and a wall (16) that separates the dispensing chamber (18) from the storage chamber. The dispensing chamber (18) includes first and second panels (24a), (24b) and a moveable collector (20) between the first and second panels (24a), (24b). Solution dispensing nozzles (26) are disposed in apertures (45) in the panels (24a), (24b), and extend from a front surface of each panel (24a), (24b). A plurality of solution supply tubes (54) extend from a rear surface of each panel (24a), (24b) to a pump (34) in the lower housing. Inner panel channels (52) are defined within each panel (24a), (24b) between the tubes (54) and the nozzles (26).

20 Claims, 11 Drawing Sheets

(51) Int. Cl.
   *B05B 16/00*    (2018.01)
   *B05B 16/40*    (2018.01)
   *B05D 1/04*     (2006.01)
   *D01D 5/00*     (2006.01)
   *D04H 1/728*    (2012.01)

(52) U.S. Cl.
   CPC ....... *A61L 2400/12* (2013.01); *B01D 2323/39* (2013.01); *D01D 5/0084* (2013.01); *D01D 5/0092* (2013.01); *D10B 2331/10* (2013.01); *D10B 2401/16* (2013.01)

(56) References Cited

U.S. PATENT DOCUMENTS

| | | |
|---|---|---|
| 9,260,803 B2 | 2/2016 | David et al. |
| 9,279,203 B2 | 3/2016 | Kim et al. |
| 2002/0122840 A1 | 9/2002 | Lee et al. |
| 2005/0233021 A1 | 10/2005 | Chun et al. |
| 2010/0112020 A1* | 5/2010 | Westbroek ........... D01D 5/0061 264/465 X |
| 2013/0168886 A1 | 7/2013 | Sumida et al. |
| 2015/0118626 A1 | 4/2015 | Yoon et al. |
| 2015/0273110 A1 | 10/2015 | McClellan et al. |
| 2016/0047075 A1 | 2/2016 | Foley et al. |
| 2016/0228892 A1* | 8/2016 | St. Peter ............... B05B 5/0533 |
| 2017/0016146 A1 | 1/2017 | Takahashi |

\* cited by examiner

SYSTEM FOR NANO-COATING A SUBSTRATE

TECHNICAL FIELD

The present disclosure relates to a system for producing polymeric nanostructures, and more particularly, to a system for nano-coating a substrate by electrospraying or electrospinning.

BACKGROUND ART

Electrospinning is a process for constructing polymeric nanofibers with diameters in the range of nanometers, while electrospraying is a similar process for making nanoparticles. The resulting nanostructures form mesh-like membranes that have very large surface area to volume ratio, high porosity and tortuosity, flexibility in surface functionalities, and can be formed from various types of polymeric solutions. Electrospinning and electrospraying are primarily used for applications such as producing advanced textiles and products demanded in the biomedical field. However, current systems of producing polymeric nanofibers and nanoparticles using existing technologies face challenges in a number of areas, including industrial viability, processing time, and low polymeric performance.

Thus, there is a demand for an industrial-scale, ecofriendly system for producing electrospun or electrosprayed products.

DISCLOSURE OF THE INVENTION

The present disclosure provides a system for nano-coating a substrate. The system includes an insulated housing having an upper hollow portion, a lower hollow portion, and a wall separating the upper hollow portion from the lower hollow portion. The upper hollow portion includes a first panel, a second panel, and a moveable collector between the first panel and the second panel. The first and second panels each include a plurality of apertures extending therethrough and a plurality of solution dispensing nozzles removably secured within the apertures. The apertures are divided into separate aperture sections by inner grooves defined in the first and second panels. Each aperture section includes different ones of the plurality of apertures and a plurality of inner panel channels connecting the apertures. The storage chamber includes additional components for electrospraying or electrospinning, including a power supply, a solution dispensing system, and a solution supply. A plurality of solution transport vessels connect the inner panel channels of each panel with the solution supply.

The solution dispensing system transports solution to the solution dispensing nozzles through the inner panel channels. The solution is discharged into the dispensing chamber through the solution dispensing nozzles. A high voltage (typically 10 kV-50 kV) current generated from the power supply is directed toward a space between the nozzle tips and the collector to form nanostructures that are deposited on the collector These and other features of the present subject matter will become readily apparent upon further review of the following specification and drawings.

BRIEF DESCRIPTION OF DRAWINGS

The drawings and detailed description which follow are intended to be merely illustrative of the exemplary embodiments and are not intended to limit the scope of the invention as set forth in the claims.

BEST MODES FOR CARRYING OUT THE INVENTION

Reference will now be made to exemplary embodiments of the present subject matter, examples of which are illustrated in the accompanying drawings. The system for nano-coating a substrate can employ electrospraying or electrospinning to provide breathable, waterproof, and/or wound healing products in a significantly reduced time. As such, the system is particularly desirable for industrial scale production of such products. The products can include, for example, textiles, apparel, and/or drug delivery products. As described in detail herein, nano-coating of a substrate by the present system can provide products that are coated with or are formed from polymeric nanostructures, e.g., nanoparticles and/or nanofibers, by electrospraying or electrospinning.

Figure 1A:
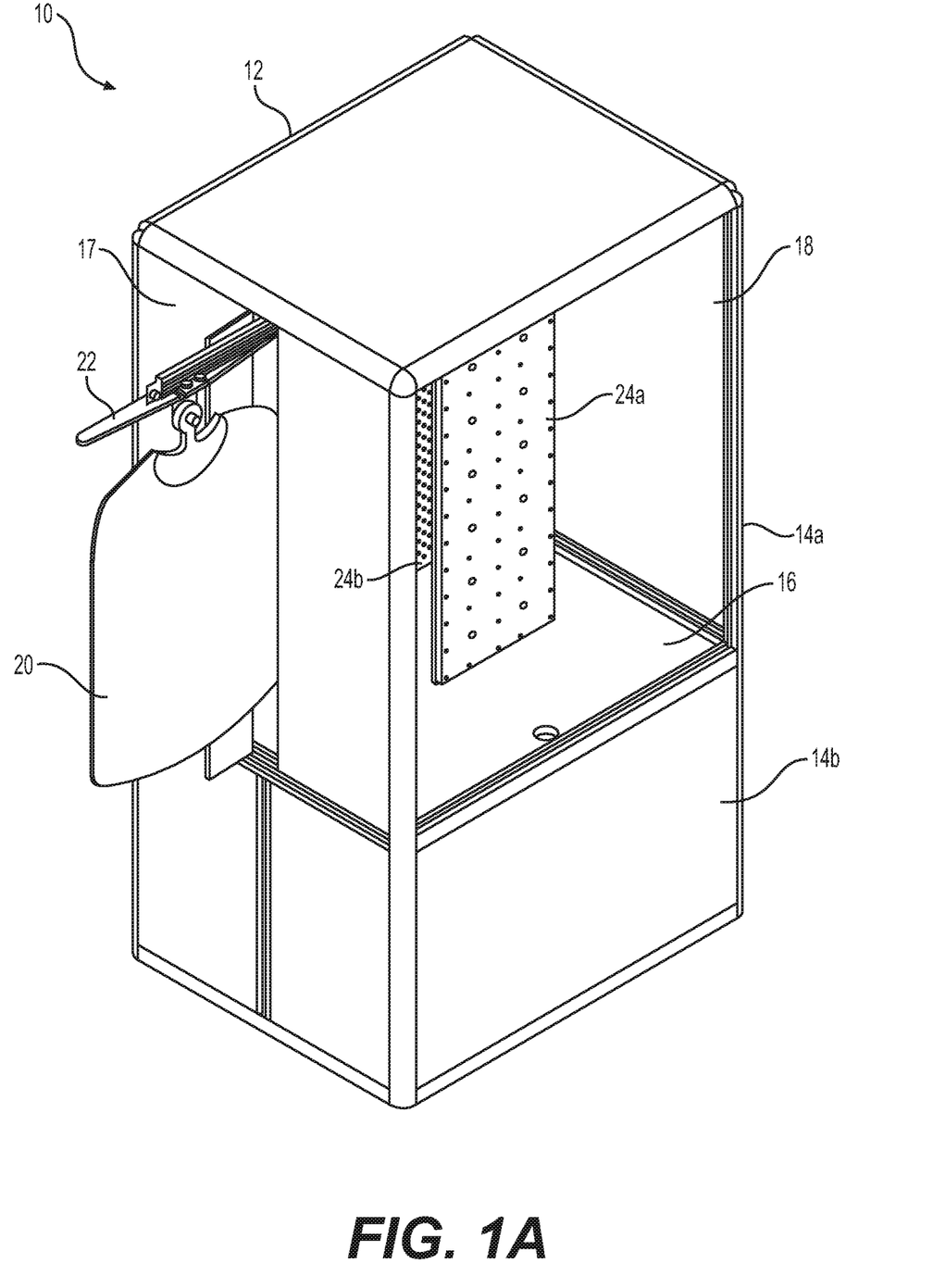
FIG. 1A is an environmental, perspective view of the system for nano-coating a substrate.
Figure 1B:
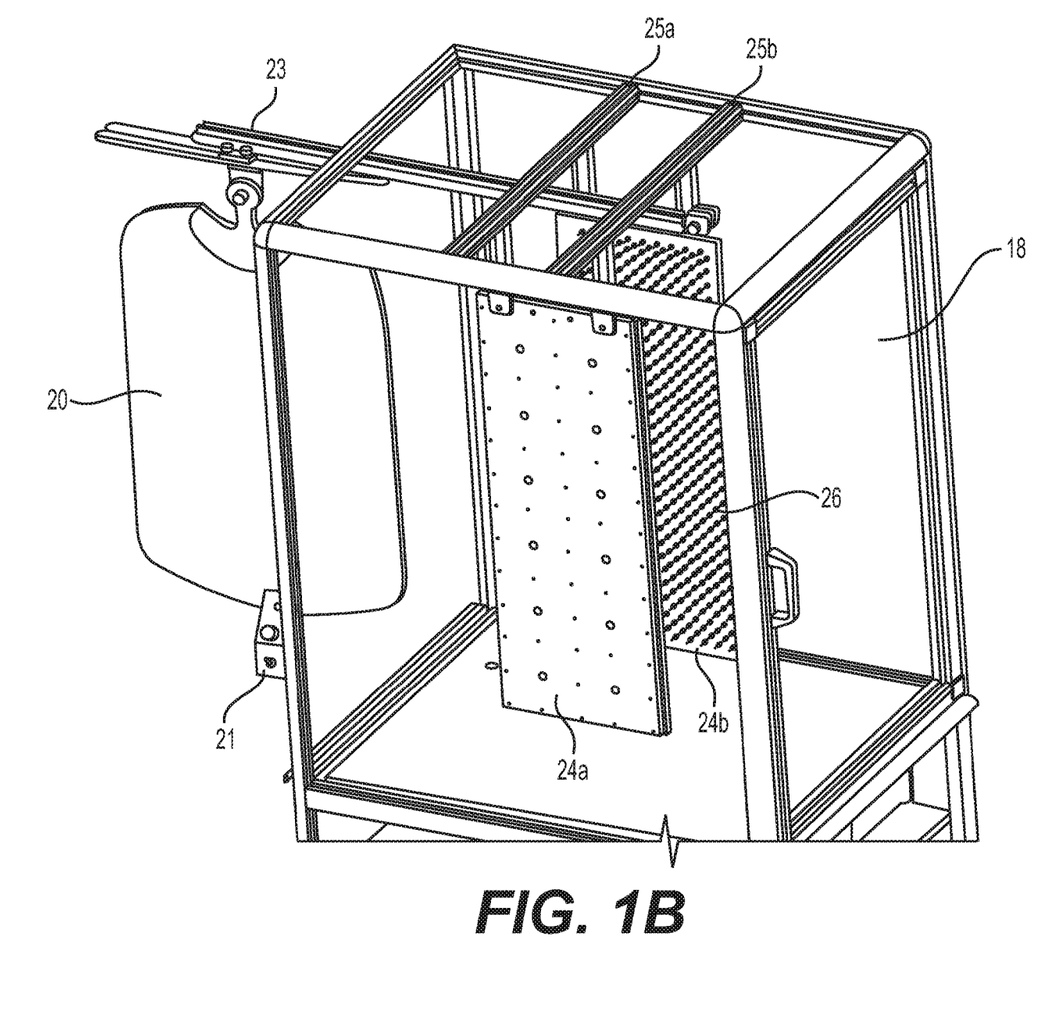
FIG. 1B is a sectional view of the system for nano-coating a substrate, showing the upper housing portion.

With reference to FIGS. 1A-1B, an exemplary system for nano-coating a substrate 10 can include an insulated housing 12 having an upper hollow portion 14a, a lower hollow portion 14b, and a wall 16 that separates the upper hollow portion 14a from the lower hollow portion 14b. The upper hollow portion 14a includes a dispensing chamber 18 in which electrospraying or electrospinning can occur. The dispensing chamber 18 includes a moveable collector 20, a linear actuator 22 connected to the collector 20, and first and second panels 24a, 24b spaced from the collector 20. The collector 20 can support a pre-fabricated product, e.g., a garment or textile, which is then coated with the nanostructures produced by electrospraying or electrospinning in the dispensing chamber. Alternatively, the nanostructures can be depositioned directly on the collector 20 to form a new product which, once formed, can be removed from the collector 20. Accordingly, the term "substrate," as used herein, can refer to the collector 20 itself or a pre-fabricated product disposed on the collector.

Figure 2A:
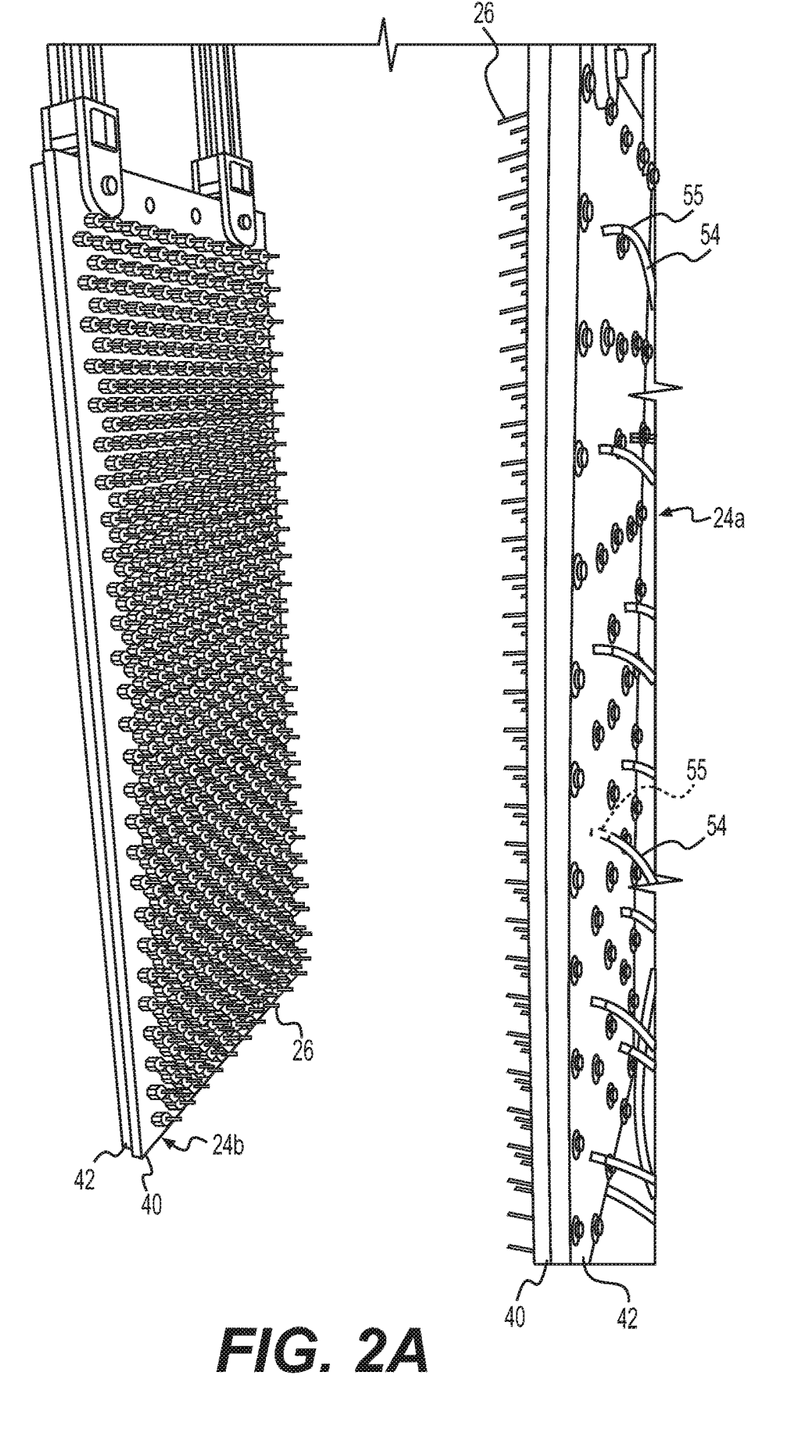
FIG. 2A is a sectional view of the system for nano-coating a substrate, showing the panels in the upper housing portion.

The linear actuator 22 functions to move the collector 20 into and out of the dispensing chamber 18, via the switch 21, as illustrated in FIG. 1B. The collector 20 can be detachably connected bto a sweeper support that is affixed to the actuator 22. A plurality of apertures 45 (FIG. 2B) extend through the panels 24a, 24b, e.g., through opposing first and second surfaces of the panels 24a, 24b. As shown in FIG. 2A, a plurality of solution dispensing nozzles 26 are removably secured, e.g., threadedly engaged, within the plurality of apertures 45.

Figure 2B:
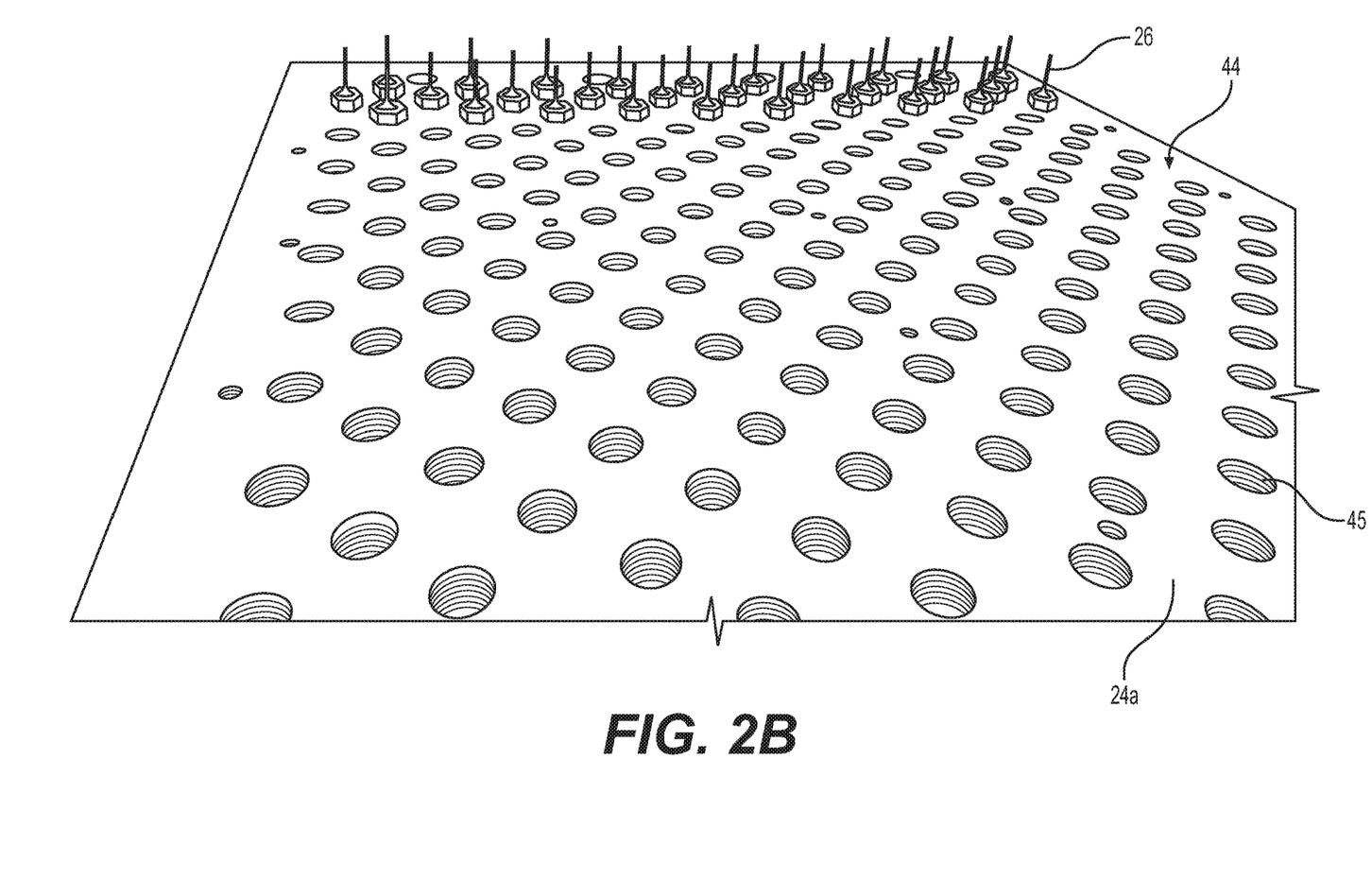
FIG. 2B is a perspective view of a front, exposed surface of an exemplary panel of the system for nano-coating a substrate.
Figure 3:
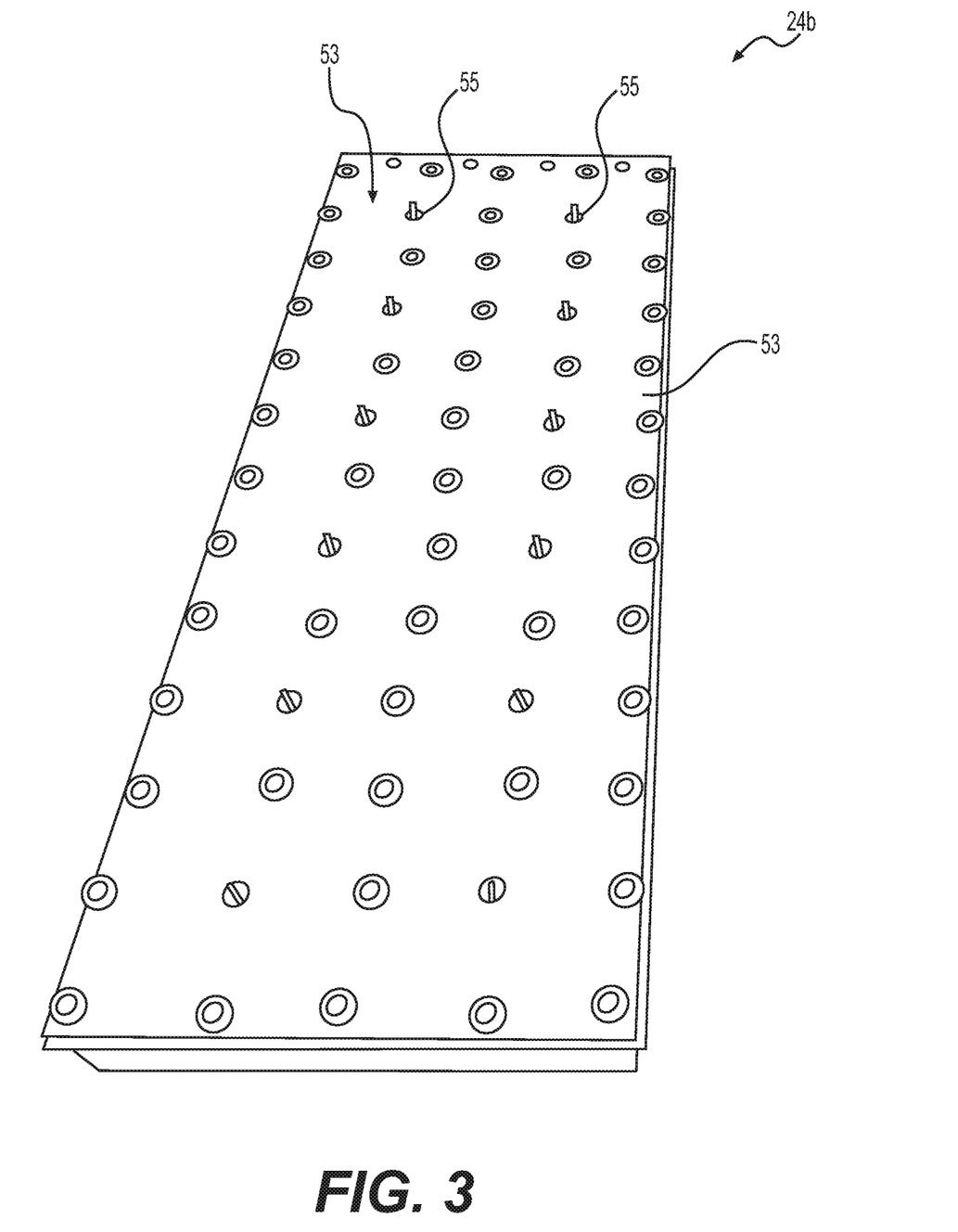
FIG. 3 is a perspective view of a rear, exposed surface of an exemplary panel of the system for nano-coating a substrate.

The panels 24a and 24b can be identical. As shown in FIG. 2A, each panel 24a, 24b preferably includes a first layer 40 and a second layer 42. The first layer 40 can be formed from metal or other electrically conductive material. The first layer 40 can include a solid aluminum breadboard, for example. Preferably, the breadboard is an anodized aluminum and allows for chemical and electrical resistance at a surface thereof. The second layer 42 can be formed from a polymeric material or other chemically, thermally, and mechanically stable material. The second layer 42 can include, for example, high-density polyethylene, polypropylene, and/or polytetrafluoroethylene. An outer surface of the first layer 40 defines a front 44 of each panel 24a, 24b (from which the nozzle needles extend) (FIG. 2B). An outer surface of the second layer 42 defines a rear 53 of each panel 24a, 24b (FIG. 3).

Figure 2C:
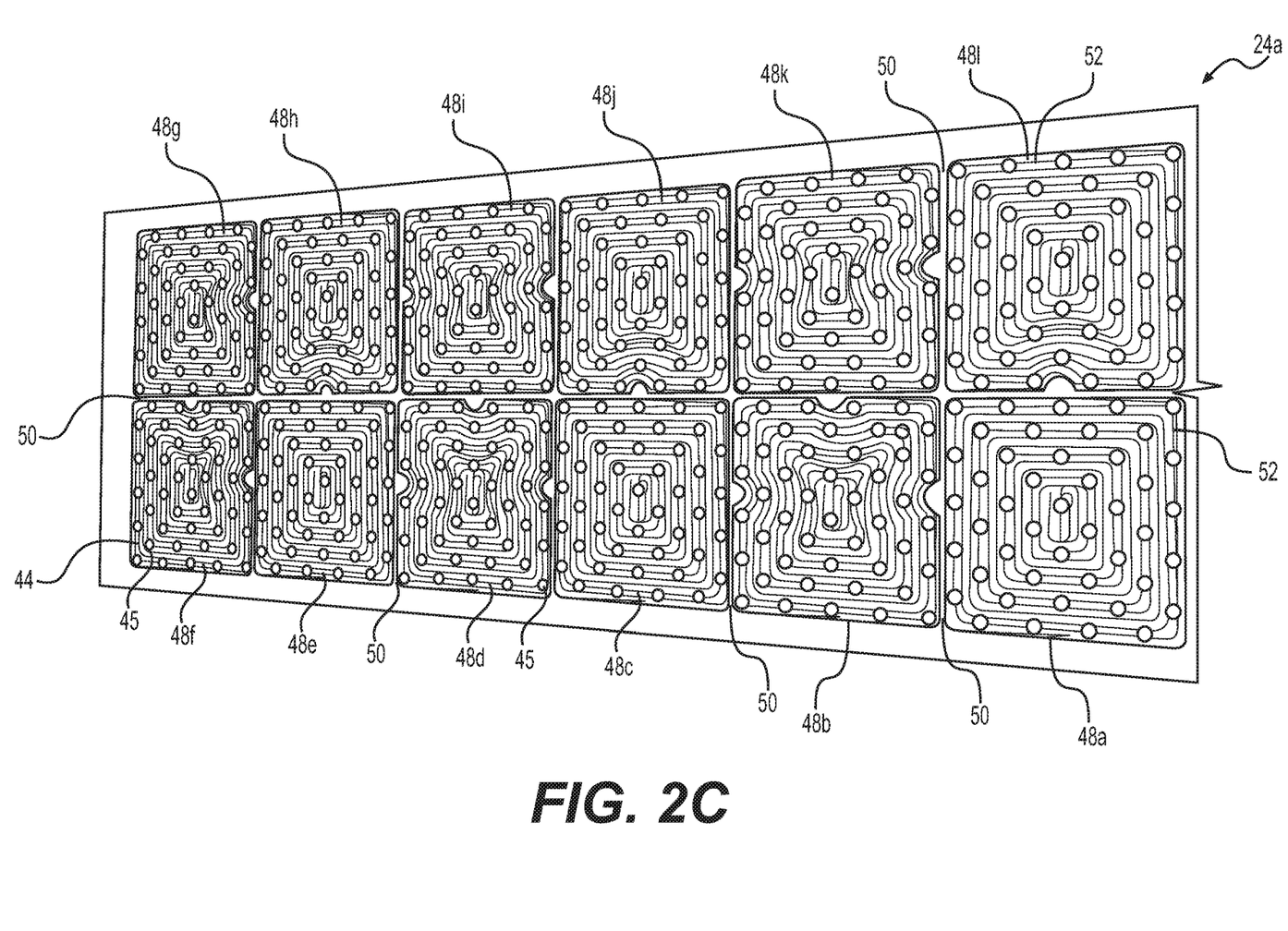
FIG. 2C is a plan view of an inner surface of an exemplary panel of the system for nano-coating a substrate.

Each panel 24a, 24b can include a plurality of inner grooves 50 defined therein, e.g., on inner surfaces of the first layer 40 and/or the second layer 42. FIG. 2C depicts the grooves 50 defined on an inner surface of the first layer 40. As shown, the grooves 50 divide the apertures 45 into a plurality of inner aperture sections 48a-48l, with each aperture section including different ones of the apertures 45. Each inner aperture section 48a-48l includes inner panel channels 52 extending between the apertures 45 of the respective section. A solution receiving-nozzle 55 can connect each aperture section 48a-48l with a solution supply tube 54 or other suitable solution transport vessel to provide solution thereto. As described in detail below and shown in FIG. 4A, solution supply tubes 54 can extend to a solution supply stored in the lower hollow portion of the housing 12. A pump 34 (FIG. 4C) or other suitable dispensing system in the lower hollow portion 14b can be operated to transport solution from the solution supply chamber 30a to the channels 52 of each section 48a-48l through the tubes 54 (FIG. 2A).

The solution dispensing nozzles 26 are preferably spinneret nozzles including a metallic hub needle with a blunt cannula end (FIG. 2B). The hub needle is fixed to a threaded hub, e.g., a Luer Lock threaded hub, that is configured for engaging threaded apertures 45 of the panel. The nozzles 26 can have the same or different gauges and dimensions. The needles of spinneret nozzles extend from each panel 24a, 24b toward the collector 20.

In operation, the solution travels from the tubes 54 to the solution dispensing nozzles 26 associated with each section through the corresponding channels 52. The solution is then discharged into the dispensing chamber 18 through the solution dispensing nozzles 26. It should be noted that one solution supply tube 54 can simultaneously provide solution to a plurality of solution dispensing nozzles 26 in an aperture section by directing solution to the channels 52 of a respective aperture section. Thus, each of the solution dispensing nozzles 26 of the present system need not be connected to or associated with a separate solution supply vessel or tube to receive solution. This permits simultaneous use of a greater number of spinneret nozzles for electrospinning and/or electrospraying than is practicably achievable by systems known in the art. The simultaneous use of a greater number of the spinneret nozzles can result in faster product coating and/or product formation times.

In the embodiment shown in FIGS. 2A, 2C and 3, each panel 24a, 24b includes twelve aperture sections 48a-48l with 45 apertures each (540 apertures total). Each panel 24a, 24b further includes twelve solution supplying tubes (one tube per aperture section) and a total of 540 spinneret nozzles. Accordingly, for the embodiment shown, the system 10 can dispense solution simultaneously from the 1080 spinneret nozzles (of both panels combined) using only twenty four solution supply tubes. It should be understood, however, that the total number of apertures, aperture sections, solution supplying tubes, and/or spinneret nozzles can be different from what is shown in the drawings as long as uniform ejection of the polymeric solution from the spinneret nozzles and deposition of the nanofibers or nanoparticles on the collector can be achieved.

The panels 24a and 24b are positioned proximate opposing surfaces of the moveable collector 20. The panels 24a and 24b can be stationary. Alternatively, the panels 24a and 24b can be configured for moving towards and away from the collector, as shown in FIG. 1B. For example, the panels 24a and 24b can be mounted on supports 25a and 25b, respectively. Also, the panels 24a and 24b can be configured to be mobile and, or tiltable to, e.g., control the tip-to-collector distance (TCD), orientation of the projected nanofibers/nanoparticles, and/or the flight time of the electrospinning stream and the vaporization time of the solvents. While two panels 24a and 24b are shown in the figures, multiple panels can be coupled together and disposed in any suitable configuration as long as uniform ejection of the polymeric solution from the spinneret nozzles and deposition of the nanofibers or nanoparticles on the collector can be achieved. The nozzles can be single axial (single cannula) nozzles or multi-axial (multi-cannula nozzles) e.g., co-axial or tri-axial nozzles. As is known, multi-axial nozzles can facilitate formation of hollow and/or core-shell fibers with various compositions. Dimensions of the sheet can be determined based on the number of nozzles needed.

Figure 4A:
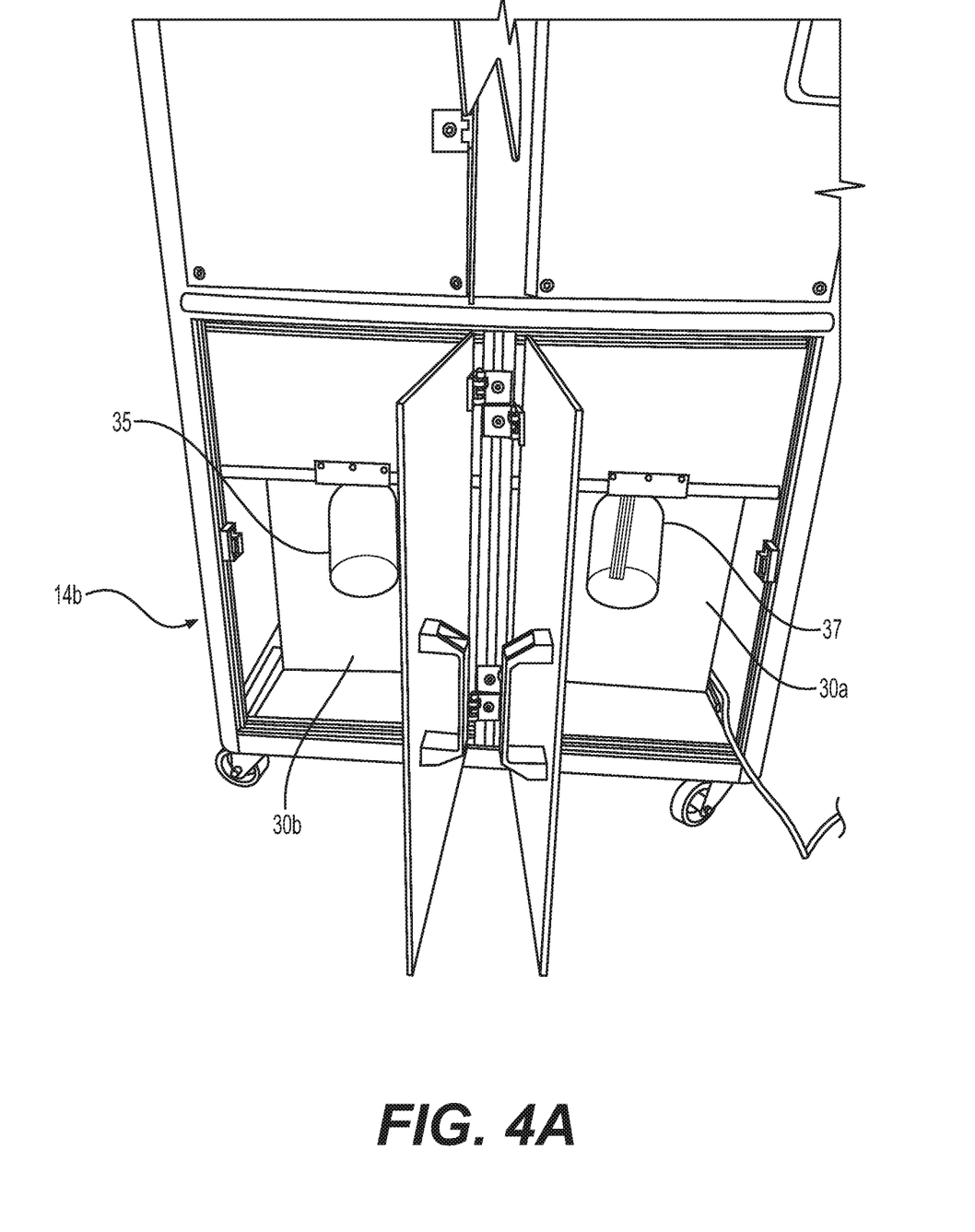
FIG. 4A is a sectional view of the system for nano-coating a substrate, showing a first side of the lower housing portion
Figure 4B:
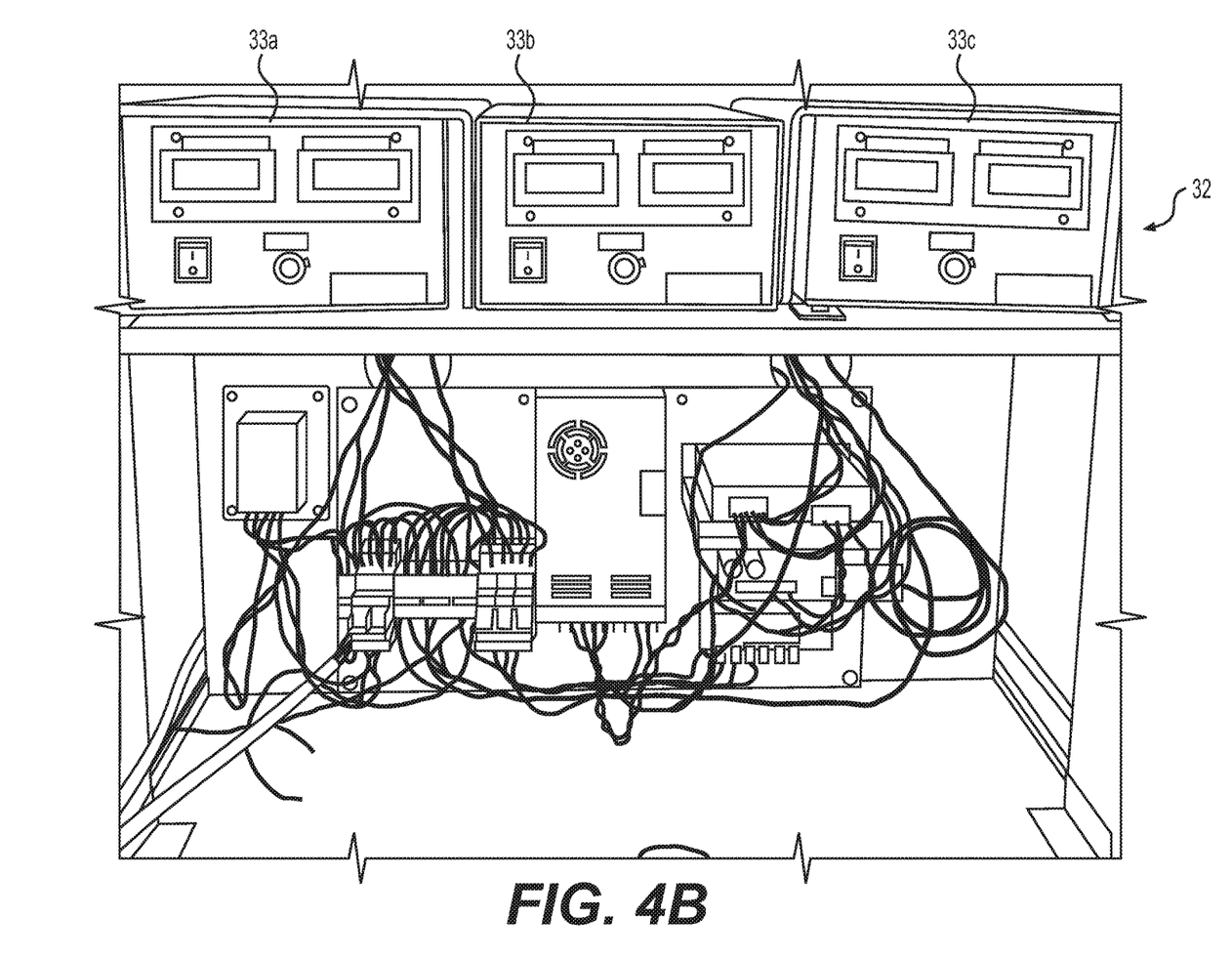
FIG. 4B is a sectional view of the system for nano-coating a substrates, showing a second side of the lower housing portion.
Figure 4C:
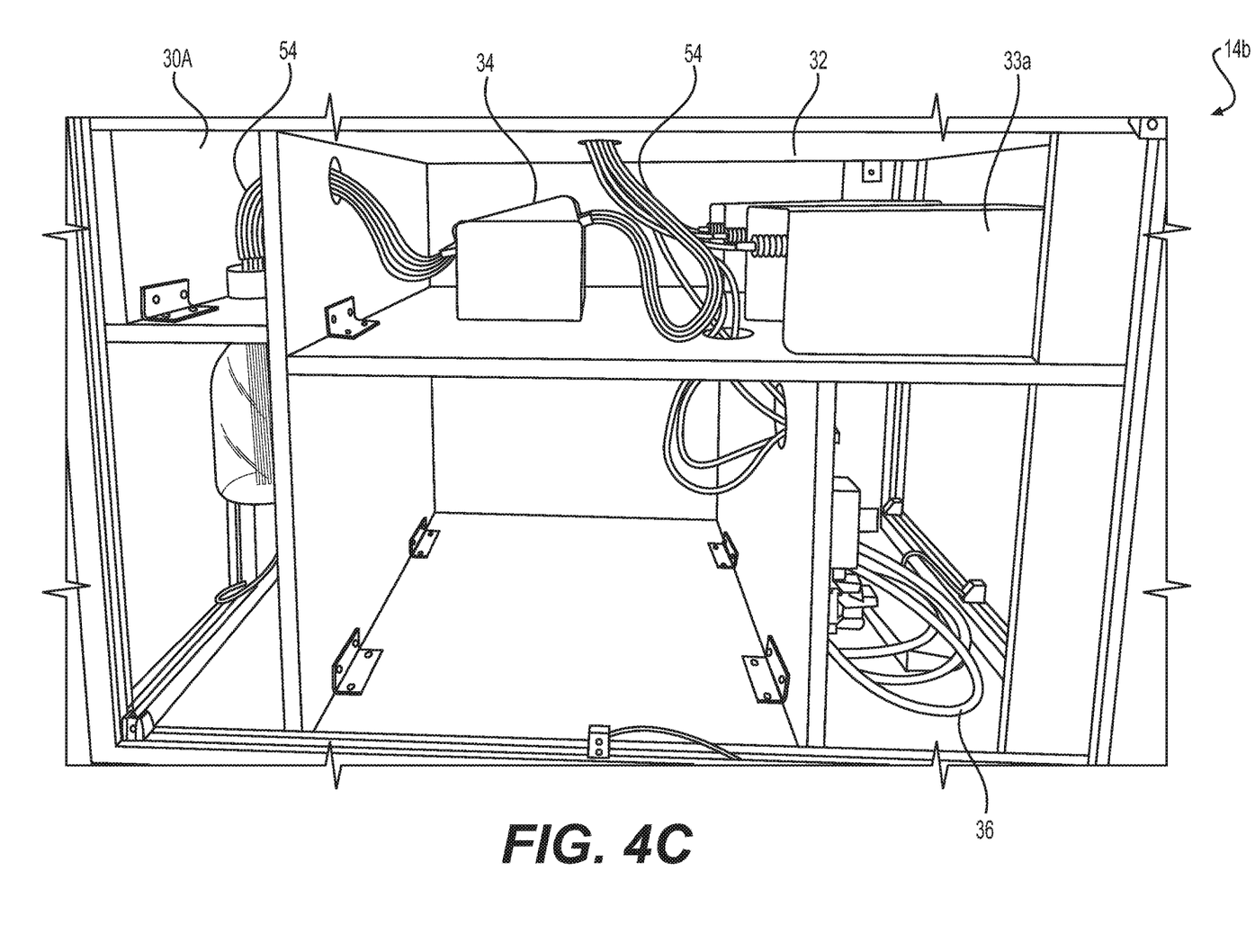
FIG. 4C is a sectional view of the system for nano-coating a substrate, showing a third side of the lower housing portion.
Figure 5:
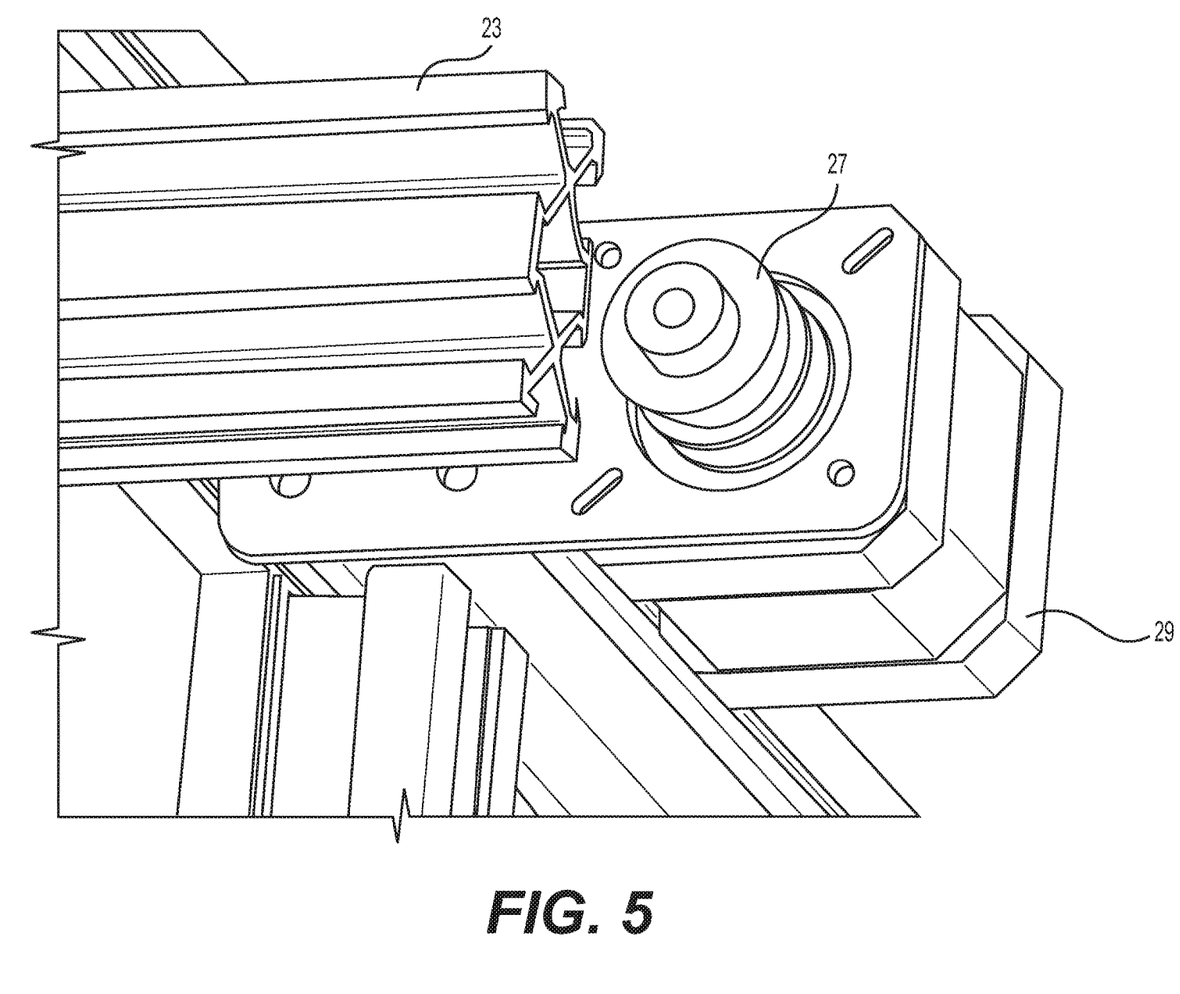
FIG. 5 is an enlarged, sectional view of the components for actuating the collector of the system for nano-coating a substrate.
Figure 6A:
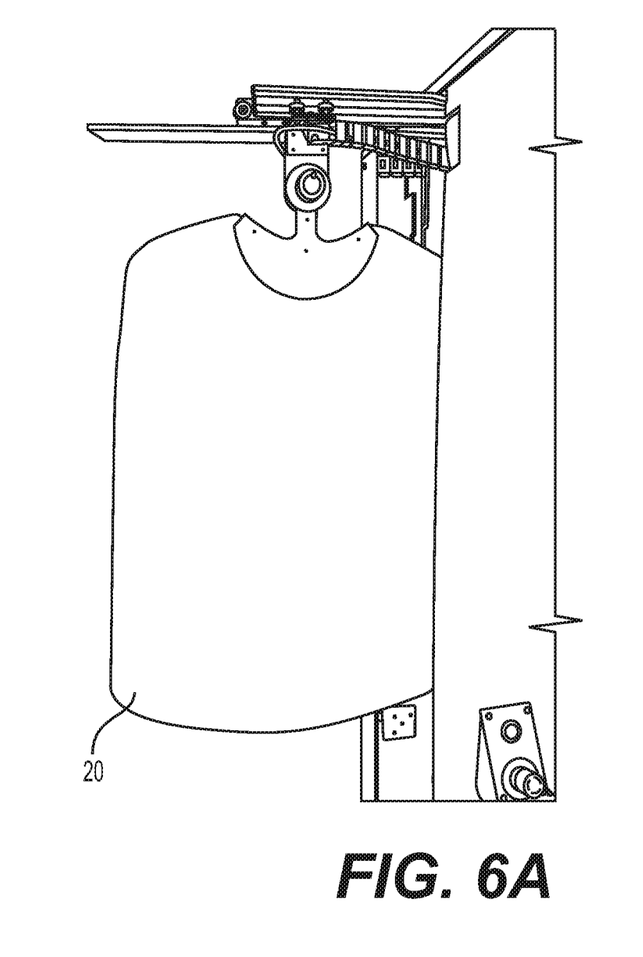
FIG. 6A is a sectional view of the system for nano-coating a substrate, showing the collector configured for supporting a shirt.
Figure 6B:
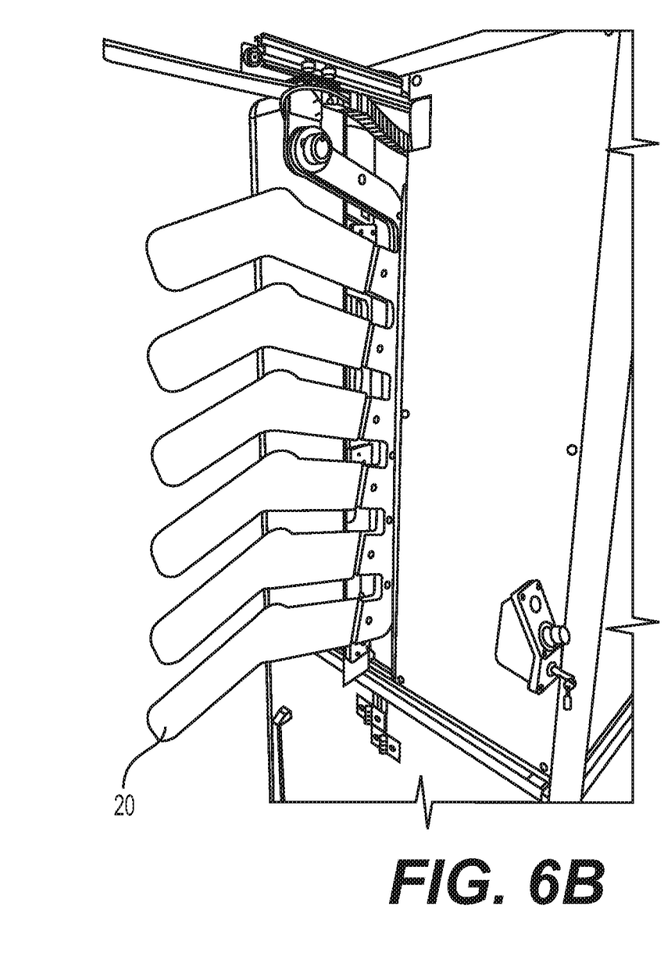
FIG. 6B a sectional view of the system for nano-coating a substrate, showing the collector configured for supporting socks.

Referring to FIGS. 4A-4C, the lower hollow portion 14b includes one or more storage chambers for housing other components known in the art for electrospraying and/or electrospinning. The lower hollow portion 14b can include, for example, a solution supply chamber 30a, at least one dispensing solution 37 in the solution supply chamber 30a, a solution recovery chamber 30b, at least one container 35 for receiving and storing recovered solution in the chamber 30b, a pump and power supply chamber 32, a pump 34 and power supply 33a-33c in the pump and power supply chamber, and an electronics and control chamber 36, for storing electronic circuitry, PBC, a microprocessor, and/or other components for electrospraying and/or electrospinning. The power supply can include multiple DC high-voltage power supplies. A high potential difference electric field can be generated through the multiple DC high-voltage power supplies. Alternatively, AC voltage power supplies may be adopted where current frequency is a considerable added factor.

Preferably, the pump 34 is a multi-channel peristaltic pump, e.g., a twenty-four channel peristaltic pump with twelve channels for each panel. In an embodiment, the pump 34 is filled with at least one viscoelastic polymeric solution. The solution is stored in the solution supply chamber 37 in a container that includes end portions of one or more tubes. Each tube extends to respective channels of the multichannel peristaltic pump 34. The multi-channeled, digital pump 34 can facilitate accelerated levels of electrospinning/electrospraying, as required for industrial applications. The multi-channel peristaltic pump 34 can be equipped with multiple rollers for minimum pulsation. The solution is extracted from the solution supply and directed to the nozzle tips by the pump. According to an embodiment, the number of channels of the multichannel peristaltic pump is equal to or less than the number of spinneret nozzles. According to an embodiment, multiple multi-channel, peristaltic pumps can be provided to deliver different polymeric solutions from several polymeric solution supply containers, simultaneously and/or successively, as desired.

The pump 34 feeds the solution to the panels 24a, 24b and the solution is then ejected from the spinneret nozzles 26 toward the collector 20 at a constant and controllable rate. Electrical charge is generated from each of the high-voltage power supplies and directed toward the solid-aluminum breadboard of the panels 24a, 24b to overcome the surface tension of the viscoelastic polymeric solution formed at the tip of each nozzle 26. The high voltage (typically 10 kV-50 kV) current is directed toward the space between the nozzle tips and the collector to form nanostructures that are deposited on the collector 20. Once electrospinning/electrospraying process is initiated, the polymeric nanofibers/nanoparticles are formed and deposited on the collector. Remaining solvent is evaporated and received in the solvent recovery system.

The pump 34 can be configured to supply the polymeric solution to the solution-receiving nozzles 55 via the appropriate solution transport vessels, e.g., 12 Pharmed BPT tubes. The transport vessels can have high chemical, electrical, and thermal resistivity. The solution supply can include one or more polymeric solutions. For example, a plurality of different storage vessels can be provided in the solution supply chamber, each holding a different polymeric solution. The pump 34 can dispense different solutions from the storage vessels in the solution supply chamber to the solution-receiving nozzles 55 at the same time or successively. The pump can be remotely operated.

The collector 20 can be anodized, negatively-charged, and/or grounded. The collector 20 can have a two-dimensional or three-dimensional structural form. According to an embodiment, the collector can support a garment thereon and the electrospraying/electrospinning conducted in the dispensing chamber can dispense nanostructures on the garment to provide breathability to the garment or render the garment waterproof. FIG. 6A depicts an embodiment in which the collector is configured to support a top or shirt. FIG. 6B depicts an embodiment in which the collector is configured to support socks. In an embodiment, the nanofibers/nanoparticles can be dispensed on both inner and outer surfaces of an apparel or product supported by the collector by disposing the garment on the collector such that the desired surface to be coated, e.g., inner or outer surface of the garment, is exposed to the solution. According to an embodiment, one or more layers of the nanofibers/nanoparticles may be dispensed on a garment to form a breathable and/or waterproof coating. Suitable polymers for providing a waterproof and breathable coating for apparels and products are provided in Maksoud et al. (2017) Electrospun Waterproof Breathable Membrane with High Level of Aerosol Filtration.

Referring to FIGS. 1A, 1B, and 5, the actuator 22 can control linear movement of the collector 20 into and out of the dispensing chamber 18 along a linear rail 23. However, the actuator can alternatively be configured for various x, y, z, u, v axes of motion. The linear actuator 22 can be in communication with a motor 26, e.g., stepper motor, and a timing pulley 27. A sweeper support can connect the collector 20 to the linear actuator 22. A sensorized door 17 can be configured to open when the collector is moving away from or into the dispensing chamber 18 and close once the collector 20 is completely within the chamber 18.

The solution supply preferably includes any appropriate electrospinning fluid or electrospraying fluid. In an embodiment, the solution supply can include a polymeric solution supply, e.g., a biodegradable/bioabsorbable polymeric solution, and a solution supply of medicinal drugs to provide nanofibers/nanoparticles impregnated with medicinal drugs, where the latter diffuse through the solid polymer matrix after which they are released into the human body tissue or structure. The rate of diffusion of the medicinal drugs out of the polymeric nanofibers/nanoparticles can be controlled by several factors, including, but not limited to the solubility of the drug itself, its diffusivity within the polymer, the polymeric nanofiber/nanoparticle diameter, type, and constituents. A plurality of different elements/agents can be incorporated in one or more polymeric solution(s). Several layers of nanofibers/nanoparticles can be dispensed in a specific configuration and controllable manner by the spinneret nozzles. Such an embodiment can be useful for developing advanced drug-delivery systems, implantable body tissue-like support systems and biodegradable/bioabsorbable polymer-based scaffolds of any desired conformation for use in biomedical applications, such as polymer-coated muscle strain socks and bandages, and wounds/burns/ulcers' dressings impregnated with different medicinal drugs, allowing controllable release of such drugs simultaneously and/or successively as required.

Particularly useful components to be added to the polymeric solutions, in addition to biodegradable/bioabsorbable polymers, such as polycaprolactone and poly-D,L-lactide, include biopolymers, such as poly-D,L-lysine and polylysine-modified poly(ethylene glycol)(PEG)-based hydrogels that are composed of FDA approved materials (Rao et al. 2011, Polylysine Modified PEG-Based Hydrogels to Enhance the Neuro-Electrode Interface). Such materials have enhanced integration with body tissues, increasing efficiency of drug-delivery and offer new ways to deliver therapeutic agents at controllable rates.

An exemplary polymeric solution can be prepared by dissolving polymeric granules in an electrically conductive solvent to form a mixture and stirring the mixture until homogenization at specific concentrations. The polymeric granules are preferably biodegradable/bioabsorbable polymers, such as polycaprolactone and/or poly-D,L-lactide. Other biopolymeric granules, such as poly-D,L-lysine, polylysine-modified poly(ethylene glycol)(PEG)-based hydrogels, and/or medicinal drugs can be added to the polymeric solution. The polymeric solution can be viscoelastic.

According to an embodiment, components of the normal extracellular matrix of human body tissues may be incorporated into the polymeric solution. For example, extracellular molecules, glycosaminoglycans (GAGs), and/or fibrous proteins, such as collagen, elastin, fibronectin, laminin can be added to the polymeric solution to provide biodegradable/bioabsorbable products. Synthetic body tissues, scaffolds, dressings, and/or organs, may be created at an industrial scale according to an embodiment. In use, cells can spontaneously adhere to the nanofibers and self-arrange into the anticipated configuration of the specific body tissue.

According to an embodiment, medicinal chemicals and/or drugs can be added to the polymeric solution, generating fibers impregnated with those agents. Medicinal agents may include proteins, hormones, enzymes, drugs, diagnostic agents such as radiosensitive nanoparticles and tracers, or any other required substance or mixture of substances having useful medical applications. Any combination of medicinal drugs may be included, for example, drugs for wounds or burns resulting from various conditions, e.g., chemical, radiation, thermal, electrical, or friction burns, diabetic ulcers, decubitus ulcers, surgical wounds, open wounds, abrasions, incisions, lacerations, or any other type of burns, wounds, or ulcers. Dressings which include biodegradable/bioabsorbable polymeric fibers impregnated with elements of the normal extracellular matrix of the human body tissues serve as tissue replacement scaffolds which allow cells to spontaneously adhere to the nanofibers and self-arrange into the anticipated configuration of the specific body tissue, as well as drug-delivery systems having customized drug release rate capabilities depending on its configuration and specific constituents.

Biodegradable/bioabsorbable polymeric surgical sutures of controllable tensile strength, impregnated with a combination of medicinal drugs, such as antibiotics and analgesics, can be produced according to the present teachings. Such products can be configured to provide customized drug release rate capabilities depending on its configuration and specific constituents.

The polymeric solution constituents may be adjusted or modified to generate nanoengineered multilayer synthetic vascular grafts to be used in surgeries such as coronary bypass heart surgeries. For example, lipophobic polymers may be integrated with anti-clot medicinal agents and drugs to prevent atherosclerotic events. In another variation, nanoengineered multilayer synthetic vascular graft may comprise an inner nanofibrous layer of biodegradable/bioabsorbable polymers, allowing growth of endothelial body cells therein, and highly porous external layer permitting communication between flowing blood cells and tissue/organ parenchyma. In a preferred embodiment, generating such vascular grafts forms a backbone for attachment of cells and presents synthetic vessels of good saturability and long-term compliancy.

The polymeric solution can include silver nanoparticles, magnesium oxide, and/or copper oxide, for forming biomedical products with antibacterial properties. In one variation, specific antibiotics and/or antifungal agents can be included to protect against different types of infections. The polymeric solution can include N, N-dimethyl formamide, tetrahydrofuran, and/or chloroform. Such solvents are highly electrically conductive, allowing creation of high potential difference electric field between the spinneret delivery panel and the negatively-charged/grounded collector. However, any other suitable solvent or mixture of solvents may be used in addition or alternatively.

Solvent vapors resulting from the electrospinning/electrospraying process collect at the top of the solution dispensing chamber and, subsequently, enter the solvent recovery chamber. The solvent recovery chamber includes a liquid vapor extraction column, a distillation unit, and a vapor recovery unit to provide a solvent. The resulting solvent is recaptured into a recovery container. In an embodiment, a chiller or any other solvent recovery system may be utilized to allow for recycling and re-usage of the process solvents in sequential electrospinning/electrospraying process cycles and further minimizing toxic emissions.

In an embodiment, the system 10 can be operated by switching a safety switch key on the control panel 21 and activating an emergency knob. The system can be configured to remain inoperative even when the safety switch is actuated, if the emergency knob has not been activated or if the sensorized-door is open. Once activated, the collector automatically comes out of the door to allow for hanging of an apparel or textile on the collector for coating. Alternatively, for creating a product composed fully of nanofibers/nanoparticles, the collector may be left exposed. The safety switch can be pressed again so that the collector enters the dispensing chamber. Once the collector is in the dispensing chamber, the door closes automatically. At this stage, the machine remains in a "stand-by" mode where one of four operating modes can be initiated: filling, electrospinning/electrospraying, suction, and cleaning. Upon activation of each of these operating modes, sequential and automatic activation of the different components occurs.

In the "filling process" mode, the high-voltage power supplies (positive and negative) are turned on, and the peristaltic pump is operated at a specific flow rate, e.g., at a maximum pump speed in a clock-wise direction. The tubings and channels are loaded with the polymeric solution being pumped up from the polymer solution supply into the respective panel spinneret nozzles. In one embodiment, and as previously mentioned, multiple polymer supply containers having different polymeric solutions with different additional agents can be provided.

In the "electrospinning/electrospraying process" mode, the high-voltage power supplies (positive and negative) remain on, and the peristaltic pump continues to operate at a specific flow rate, e.g., less than maximum speed this time in a clock-wise direction. Alternatively, the peristaltic pump flow rate may be changed according to the electrospinning/electrospraying end-product parameters. In an embodiment, during this operating mode, two cycles of electrospinning/electrospraying processes may be performed to enable coating of both the face (outer surface) and the base (inner surface) of the apparel, product, and/or drug-delivery system. In one variation, several cycles of electrospinning/electrospraying processes may be employed so as to allow for creation of several layers of nanofibers/nanoparticles on the apparel, product, or drug-delivery system being coated or produced.

During the "electrospinning/electrospraying process" mode, the sweeping speed, direction, and starting/end-point of the collector (controlled by the stepper motor) may be changed or modified as desired. In an embodiment, the stepper motor is automatically controlled by limiting switches disposed along the actuator's linear rail.

In the "suction process" mode, the high-voltage power supplies (positive and negative) are turned off, while the pump remains on at a specific flow rate, e.g., at a maximum pump speed in anti-clock wise direction. In this mode, the polymeric solution is cleared out of the machine tubings and is directed back into the polymer solution supply container.

In the "cleaning process" mode, the high-voltage power supplies (positive and negative) are turned off, while the digital-remoted multichannel peristaltic pump remains on at a specific flow rate, e.g., a maximum pump speed in a clock-wise direction. In this mode, cleaning solvent alone is pumped up from a cleaning solvent container and loaded into the tubings and channels of the spinneret delivery system, so that the spinneret nozzles are now occupied with the solvent solution. In a preferred embodiment, several processes of suction and cleaning can be employed to ensure unloading or emptying of the machine tubings and channels from the polymeric solution.

The following examples are given by way of illustration, and should not be construed to limit the scope of the present invention.

Example 1

Coating for Apparel

T-shirt and socks were coated on both inner and outer surfaces with polymeric nanofibers composed of super hydrophobic polymers using the present system. The polymeric solution was prepared by dissolving polyurethane (PU) into dimethylformamide (DMF) solvent. The resulting garments were waterproof, breathable, and exhibited a high degree of aerosol filtration.

Example 2

Medicament Incorporated in Wound Dressings

Waterproof, breathable, protective dressings for burns, wounds, and ulcers, impregnated with multiple medicinal drugs, were produced by coating the outer surface of the dressings with polymeric nanofibers composed of super hydrophobic polymers, and the inner surface with biodegradable/bioabsorbable nanofibers loaded with the desired drugs. The polymeric solution for the outer surface was prepared by dissolving polyurethane (PU) into dimethylformamide (DMF) solvent. The polymeric solution for the inner surface was prepared by dissolving polycaprolactone (PCL) into dimethylformamide (DMF) solvent mixed with a combination of three drugs having anti-inflammatory, analgesic, and antibiotic properties, namely β-sitosterol (Sigma, USA), silver(I) sulfadiazine (Sigma, USA), and acetaminophen (Sigma, USA). β-sitosterol is a phytosterol usually applied to the skin for treating wounds and burns, to provide anti-inflammatory and healing properties. Silver(I) sulfadiazine is a sulfa antibiotic that helps prevent and treat wound infections in cases of serious burns, by halting bacterial growth that may infect the wounded or burned area. Finally, acetaminophen treats mild to moderate pain.

In a first step, the T-shirt was disposed on the collector to expose an outer surface thereof and the collector was actuated to move completely into the dispensing chamber. The solution of PU/DMF was electrosprayed on the outer surface of the T-shirt for a duration of 10 seconds to coat the T-shirt with the polyurethane super hydrophobic polymeric nanofibers. The collector was then moved out of the dispensing chamber. The T-shirt was removed from the collector, turned inside out, and repositioned on the collector so that its inner surface was exposed. The collector was actuated to move completely into the dispensing chamber. A solution of polycaprolactone/dimethylformamide/tetrahydrofuran impregnated with β-sitosterol, silver (I) sulfadiazine, and acetaminophen was electrosprayed on the inner surface of the T-shirt for a duration 378 seconds.

Example 3

Medicament Incorporated in Bandages

Waterproof-breathable, protective bandages impregnated with multiple medicinal drugs, were produced by coating the outer surface of the bandages with polymeric nanofibers including super hydrophobic polymers, and the inner surface with biodegradable/bioabsorbable nanofibers loaded with the desired drugs. The polymeric solution for the outer surface was prepared by dissolving polyurethane (PU) into dimethylformamide (DMF) solvent. The polymeric solution for the inner surface was prepared by dissolving polycaprolactone (PCL) into dimethylformamide (DMF) solvent mixed with a combination of two drugs having anti-inflammatory and analgesic properties, namely ketoprofen (Sigma, USA) and acetaminophen (Sigma, USA). Ketoprofen is a nonsteroidal anti-inflammatory drug (NSAID) prescribed usually for different pathology-related inflammatory pains.

It is to be understood that the present subject matter is not limited to the embodiments described above, but encompasses any and all embodiments within the scope of the following claims.

I claim:

1. A system for nano-coating a substrate, comprising:
    an insulated housing, the housing including an upper hollow portion, a lower hollow portion, and a wall separating the upper hollow portion from the lower hollow portion;
    a first panel and a second panel in the upper hollow portion, the first panel and the second panel each including a plurality of apertures extending therethrough and a plurality of solution dispensing nozzles removably secured within the apertures, the apertures being divided into separate aperture sections by inner grooves defined in inner surfaces of the first and second panels, each aperture section including different ones of the plurality of apertures and a plurality of inner panel channels connecting the apertures;
    a collector moveably positioned in the upper hollow portion, between the first panel and the second panel;
    a plurality of solution transport vessels, each solution transport vessel being connected to a different aperture section;
    at least one storage chamber in the lower hollow portion, the at least one storage chamber including a power supply, a solution dispensing system, and a solution supply, the solution supply being in contact with the plurality of solution transport vessels.

2. The system for nano-coating a substrate according to claim 1, wherein the solution dispensing system comprises a pump.

3. The system for nano-coating a substrate according to claim 2, wherein the pump comprises a multi-channel peristaltic pump.

4. The system for nano-coating a substrate according to claim 1, wherein the plurality of solution transport vessels comprise a plurality of tubes.

5. The system for nano-coating a substrate according to claim 1, wherein the first and second panels each include a first, electrically conductive layer and a second, thermally stable layer.

6. The system for nano-coating a substrate according to claim 5, wherein the first layer includes a metal.

7. The system for nano-coating a substrate according to claim 6, wherein the metal is aluminum.

8. The system for nano-coating a substrate according to claim 5, wherein the second layer includes at least one of polyethylene, polypropylene, and polytetrafluoroethylene.

9. The system for nano-coating a substrate according to claim 1, wherein the first panel and the second panel are stationary.

10. The system for nano-coating a substrate according to claim 1, wherein the solution dispensing nozzles include spinneret nozzles, each spinneret nozzle having a hub needle extending from a threaded hub, the threaded hub of each nozzle threadedly engaging a respective aperture in the panels, the needle of each nozzle directed toward the collector.

11. The system for nano-coating a substrate according to claim 10, wherein the spinneret nozzles include at least one of a single axial nozzle and a multi-axial nozzle.

12. The system for nano-coating a substrate according to claim 1, further comprising a solvent recovery vessel in the lower housing portion.

13. A method of nano-coating a substrate using the system of claim 1, comprising:
moving the collector into the upper hollow portion;
transporting the solution to the solution dispensing nozzles through the inner panel channels;
ejecting the transported solution from the nozzles toward the collector;
directing a high voltage current toward an area between the nozzles and the collector to form nanostructures;
receiving the nanostructures on the collector.

14. The method of nano-coating a substrate according to claim 13, further comprising:
depositing a garment on the collector before moving the collector into the dispensing chamber.

15. The method of nano-coating a substrate using the system of claim 13, further comprising depositing a textile on the collector before moving the collector into the dispensing chamber.

16. A system for nano-coating a substrate, comprising:
an insulated housing, the housing including an upper hollow portion, a lower hollow portion, and a wall separating the upper hollow portion from the lower hollow portion;
a first stationary panel and a second stationary panel in the upper hollow portion, the first panel and the second panel each including a plurality of apertures extending therethrough and a plurality of spinneret nozzles removably secured within the apertures, the apertures being divided into separate aperture sections by inner grooves defined in the first and second panels, each aperture section including different ones of the plurality of apertures and a plurality of inner panel channels connecting the apertures;
a collector moveably positioned in the upper hollow portion, between the first panel and the second panel;
a plurality of tubes, each tube being connected to a different aperture section;
at least one storage chamber in the lower hollow portion, the at least one storage chamber including a power supply, a pump, and a solution supply, the solution supply being in contact with the plurality of tubes.

17. The system for nano-coating a substrate according to claim 16, wherein the pump comprises a multi-channel peristaltic pump.

18. The system for nano-coating a substrate according to claim 16, wherein the first and second panels each include a first, electrically conductive layer and a second, thermally stable layer.

19. The system for nano-coating a substrate according to claim 16, wherein the first layer comprises aluminum and the second layer comprises at least one of polyethylene, polypropylene, and polytetrafluoroethylene.

20. The system for nano-coating a substrate according to claim 16, further comprising a solvent recovery vessel in the lower housing portion.

* * * * *